United States Patent
Hung

(10) Patent No.: US 9,636,465 B2
(45) Date of Patent: May 2, 2017

(54) SAFETY SYRINGE

(71) Applicants: Bo-Ren Jheng, Taichung (TW); Yih Hoong Enterprise Co., Ltd., Hsinchu (TW)

(72) Inventor: Chih-Kuo Hung, Hsinchu (TW)

(73) Assignees: Bo-Ren Jheng, Taichung (TW); YIH HOONG ENTERPRISE CO., LTD., Hsinchu (TW)

( * ) Notice: Subject to any disclaimer, the term of this patent is extended or adjusted under 35 U.S.C. 154(b) by 226 days.

(21) Appl. No.: 14/552,185

(22) Filed: Nov. 24, 2014

(65) Prior Publication Data

US 2015/0151056 A1 Jun. 4, 2015

(30) Foreign Application Priority Data

Nov. 29, 2013 (TW) .............................. 102143887 A

(51) Int. Cl.
*A61M 5/32* (2006.01)
*A61M 5/34* (2006.01)
*A61M 5/178* (2006.01)
*A61M 5/50* (2006.01)
*A61M 5/315* (2006.01)

(52) U.S. Cl.
CPC .......... *A61M 5/3221* (2013.01); *A61M 5/178* (2013.01); *A61M 5/322* (2013.01); *A61M 5/344* (2013.01); *A61M 5/50* (2013.01); *A61M 2005/31516* (2013.01); *A61M 2005/323* (2013.01); *A61M 2005/3231* (2013.01)

(58) Field of Classification Search
CPC .......... A61M 2005/31516; A61M 2005/3231; A61M 5/178; A61M 5/3221; A61M 5/344; A61M 5/345; A61M 5/50
See application file for complete search history.

(56) References Cited

U.S. PATENT DOCUMENTS 6,193,687 B1 * 2/2001 Lo ........................ A61M 5/322
604/110
6,423,033 B1 7/2002 Tsai
(Continued)

FOREIGN PATENT DOCUMENTS

CN 2782120 Y 5/2006
TW M286674 U 2/2006
(Continued)

*Primary Examiner* — Quynh-Nhu H Vu
(74) *Attorney, Agent, or Firm* — Muncy, Geissler, Olds & Lowe, P.C.

(57) ABSTRACT

A safety syringe includes a barrel having a positioning groove, a needle holder mounted in the barrel and having a first internal flange engaged in the positioning groove of the barrel and a first positioning flange, an interlocking seat mounted in the needle holder and having an elastic flap and a first external flange, and a plunger mounted in the barrel and having a second external flange. By means of engagement between the elastic flap of the interlocking seat and the second external flange of the plunger, the interlocking seat can be pulled by the plunger to let the first external flange to be forced into engagement with the first internal flange of the needle holder for allowing the needle holder with an attached needlestick to be pulled backwardly into the inside of the barrel to assure the safety of the syringe after the injection.

6 Claims, 7 Drawing Sheets

(56) References Cited

U.S. PATENT DOCUMENTS

| | | | |
|---|---|---|---|
| 6,488,657 B1* | 12/2002 | Lo | A61M 5/322 604/110 |
| 6,752,784 B2* | 6/2004 | Tsai | A61M 5/322 604/110 |
| 2003/0083627 A1 | 5/2003 | Chen | |
| 2004/0122378 A1 | 6/2004 | Hsu | |
| 2008/0132837 A1* | 6/2008 | Lin | A61M 5/322 604/110 |

FOREIGN PATENT DOCUMENTS

| | | |
|---|---|---|
| TW | M340060 U | 9/2008 |
| TW | 201039877 A1 | 11/2010 |
| TW | 21100133 A1 | 1/2011 |
| TW | M448282 U | 3/2013 |
| TW | M483802 U | 8/2014 |

* cited by examiner

SAFETY SYRINGE

BACKGROUND OF THE INVENTION

1. Field of the Invention

The present invention relates to medical equipment and more particularly, to a safety syringe.

2. Description of the Related Art

A syringe is an implement adapted for use with a needlestick to inject a liquid medicine, blood or other nutrient solution into the human body. After the injection, the needlestick has the human blood adhered thereto. Therefore, the needlestick should be disposed of safety after the use, avoiding medicare personnel or other persons from being injured by the needlestick accidentally.

The most commonly applied method for disposal of a used needlestick is to insert the needlestick into a needlestick cap after its use. However, when the medicare personnel inserts the needlestick into a needlestick cap, the hand of the medicare personnel can be injured by the needlestick accidentally due to their own carelessness or by other external forces, increasing the risk of infection.

SUMMARY OF THE INVENTION

The present invention has been accomplished under the circumstances in view. It is the main object of the present invention to provide a safety syringe, which is easy to operate and can accurately receive the needlestick after its use, reducing the risk of accidental needlestick injuries.

To achieve this and other objects of the present invention, a safety syringe comprises a barrel, a needle holder, an interlocking seat, and a plunger. The barrel comprises a barrel body, a tubular neck outwardly extending from one end of the barrel body, and a positioning groove extending around an inside wall of the tubular neck. The needle holder is detachably mounted in the tubular neck of the barrel, comprising a first ring wall, a first internal flange located in the first ring wall, and a first positioning flange located at one end of the first ring wall and elastically engaged in the positioning groove inside the tubular neck of the barrel. The interlocking seat is axially movably mounted in the first ring wall of the needle holder, comprising a second ring wall, at least one elastic flap mounted in the second ring wall, and a first external flange located at one end of the second ring wall for engagement with the first internal flange of the needle holder by means of an axial movement of the interlocking seat. The plunger is axially movably mounted in the barrel body of the barrel, comprising a pressing portion inserted into the inside of the second ring wall of the interlocking seat and a second external flange located at an outer surface of the pressing portion and adapted for engagement with the elastic flaps of the interlocking seat upon an axial movement of the plunger relative to the barrel. Thus, the interlocking seat can be moved by a pull force of the plunger in direction away from the needle holder to carry the needle holder and an attached needlestick into the inside of the barrel.

Preferably, the needle holder further comprises an end wall located at an opposite end of the first ring wall, and a second internal flange extending around an inner surface of the first ring wall. The second internal flange is disposed between the first internal flange and the end wall. Thus, when mounting the interlocking seat in the needle holder, the first external flange can be forced into engagement with the second internal flange to achieve a good positioning effect.

Preferably, the interlocking seat comprises two slots located in the second ring wall, and two elastic flaps respectively mounted in the two slots. Further, the distance between these two elastic flaps is smaller than the outer diameter of the second external flange at the pressing portion of the plunger. Thus, during the injection, the two elastic flaps of the interlocking seat are forced to expand by the second external flange at the pressing portion of the plunger for enabling the pressing portion to pass over. After the second external flange passed over the elastic flaps of the interlocking seat, the elastic flaps of the interlocking seat immediately return to their former shape and are stopped against the second external flange at the pressing portion of the plunger.

Preferably, the interlocking seat further comprises a second positioning flange located at an opposite end of the second ring wall and stopped against the first positioning flange of the needle holder to elastically deform the first positioning flange of the needle holder and to force it into the positioning groove of the barrel.

Preferably, the plunger has a bottom end thereof mounted with an elastic stopper. The elastic stopper comprises a buffer portion at a top end thereof. Thus, when the buffer portion is stopped at the second positioning flange, a further force should be employed to force the elastic flaps into engagement with the second external flange.

Other advantages and features of the present invention will be fully understood by reference to the following specification in conjunction with the accompanying drawings, in which like reference signs denote like components of structure.

DETAILED DESCRIPTION OF THE INVENTION

Figures 1, 1A:
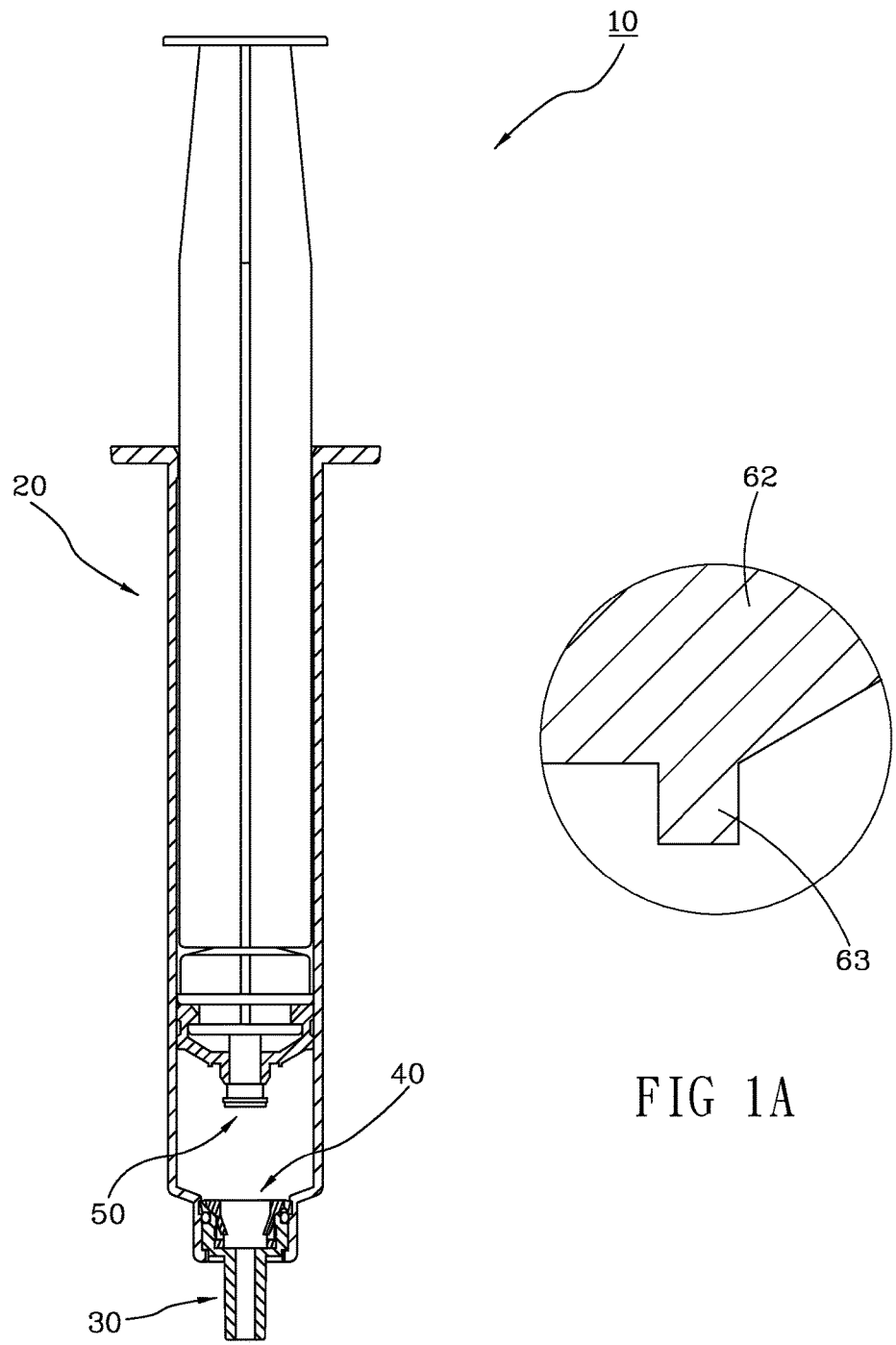
FIG. 1 is a sectional assembly view of a safety syringe in accordance with the present invention.
FIG. 1A is an enlarged view of a part of FIG. 1, illustrating the configuration of the buffer portion at the elastic stopper.
Figure 2:
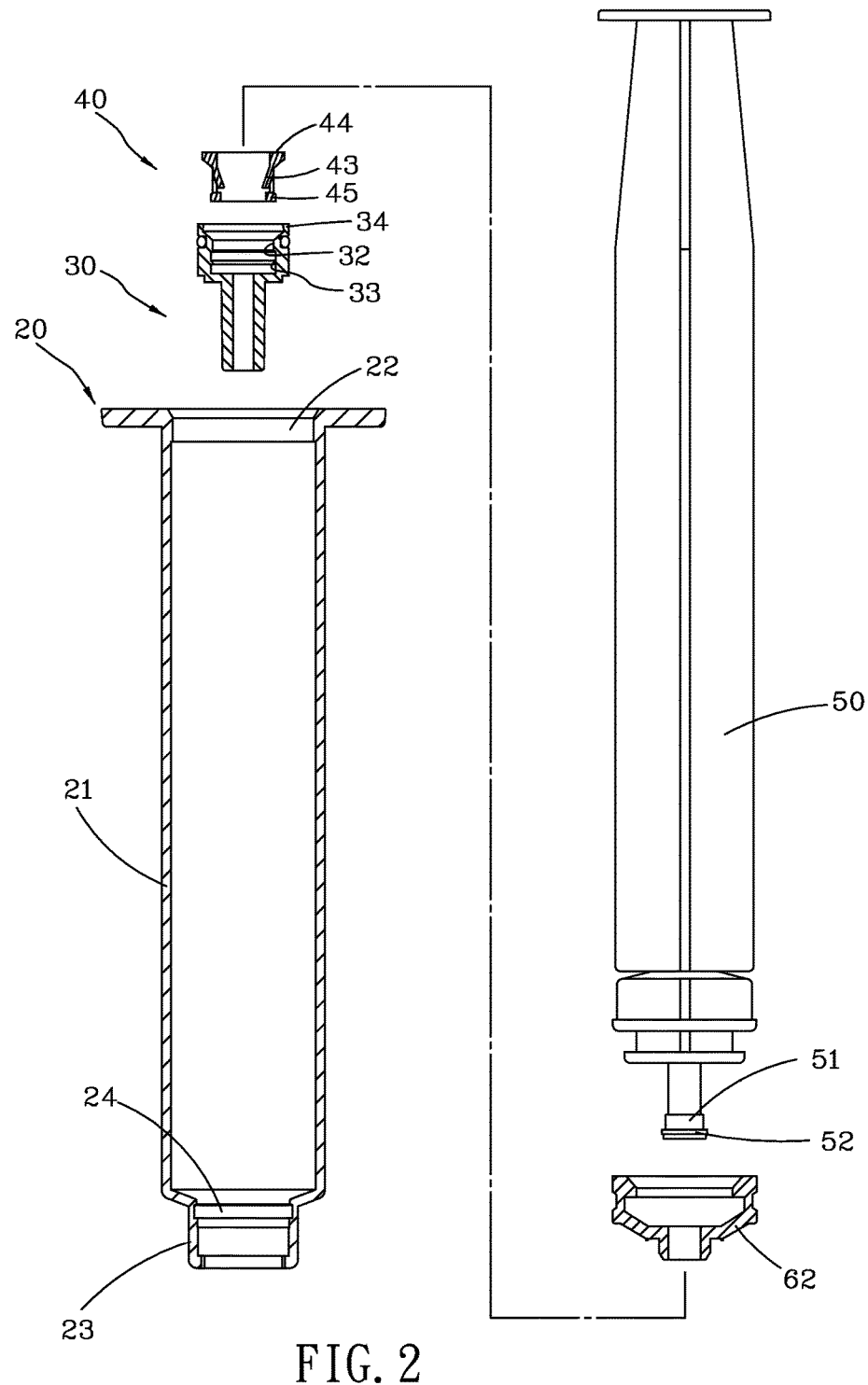
FIG. 2 is a sectional exploded view of the safety syringe in accordance with the present invention.

Referring to FIGS. 1 and 2, a safety syringe 10 in accordance with the present invention is shown. The safety syringe 10 comprises a barrel 20, a needle holder 30, an interlocking seat 40, and a plunger 50.

The barrel 20 comprises a barrel body 21, an opening 22 located in a top end of the barrel body 21, a tubular neck 23 forwardly extending from an opposing bottom end of the barrel body 21, and a positioning groove 24 extending around an inside wall of the tubular neck 23.

Figure 3:
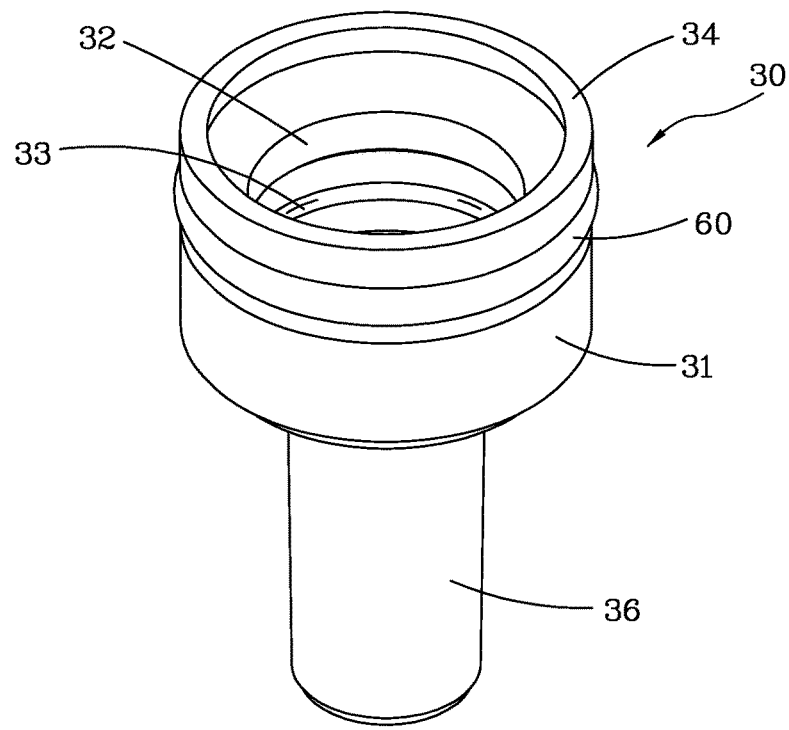
FIG. 3 is an elevational view of the needle holder in accordance with the present invention.
Figure 4:
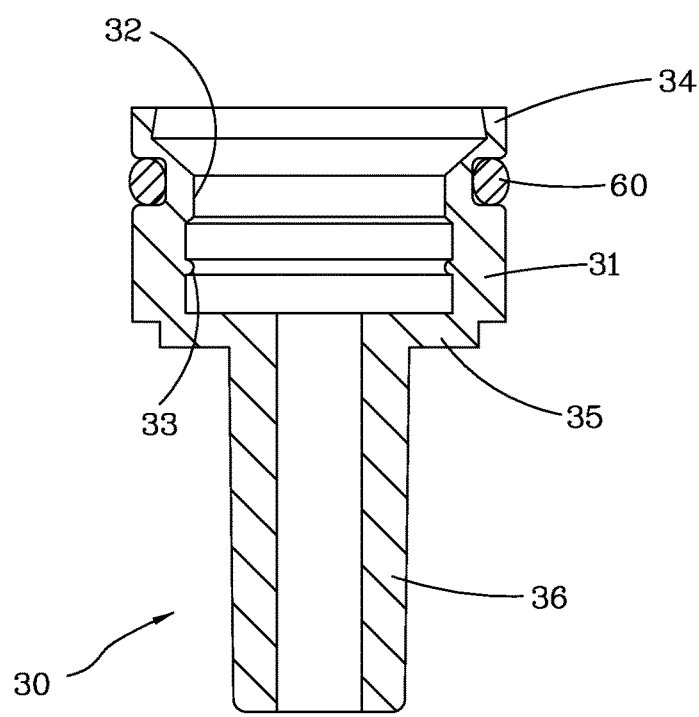
FIG. 4 is a sectional view of the needle holder in accordance with the present invention.

Referring to FIGS. 3 and 4, the needle holder 30 is adapted for the mounting of a needlestick (not shown), comprising a first ring wall 31, a first internal flange 32 and a second internal flange 33. The first internal flange 32 and the second internal flange 33 extend around an inner surface of the first ring wall 31 and spaced from each other at a distance. Further, the inner diameter of the first internal flange 32 is smaller than the inner diameter of the second internal flange 33. Further, a leak-proof gasket ring 60 is mounted around the outer surface of the first ring wall 31. The needle holder 30 further comprises a first positioning flange 34 radially outwardly extending from a top end of the first ring wall 31 and having an outer diameter larger than the outer diameter of the first internal flange 32 and the outer diameter of the second internal flange 33, an end wall 35 located at an opposing bottom end of the first ring wall 31 and spaced from the second internal flange 33 at a distance smaller than the distance between the end wall 35 and the first internal flange 32, and a tubular wall 36 outwardly extending from the end wall 35 in direction away from the first ring wall 31.

Figure 5:
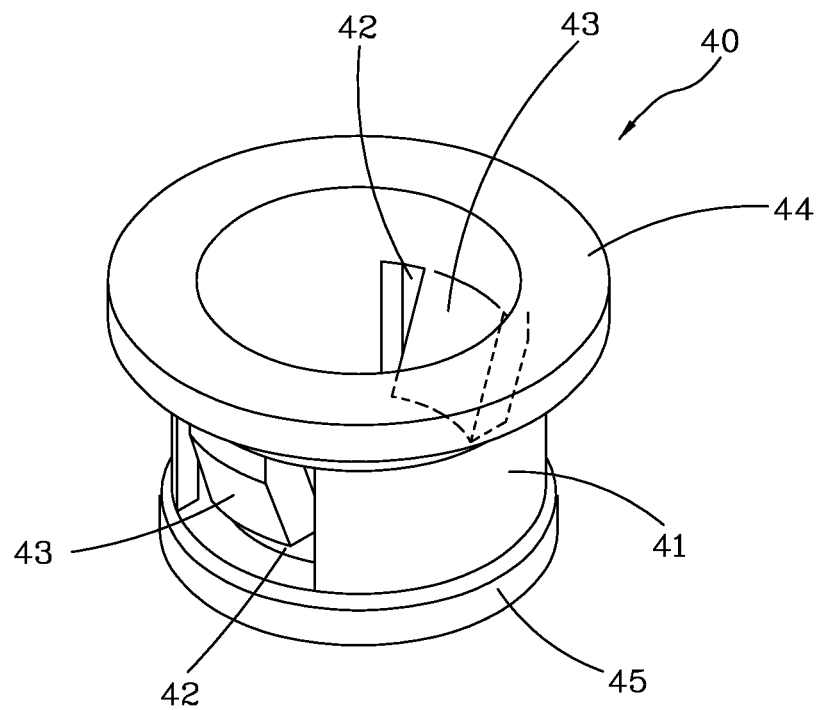
FIG. 5 is an elevational view of the interlocking seat in accordance with the present invention.
Figure 6:
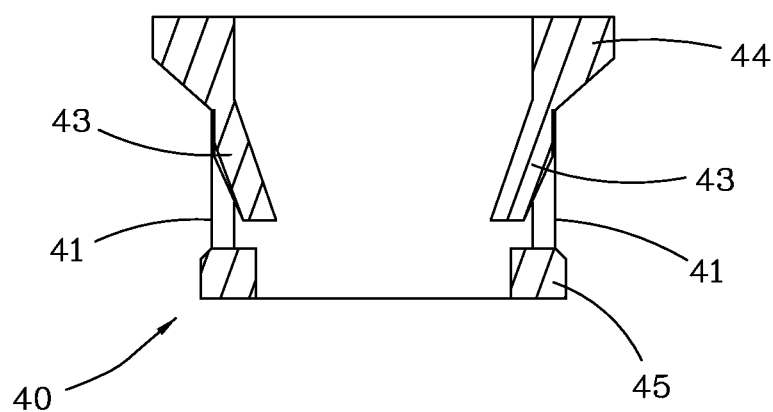
FIG. 6 is a sectional view of the interlocking seat in accordance with the present invention.

Referring to FIGS. 5 and 6, the interlocking seat 40 comprises a second ring wall 41, two slots 42 located in the second ring wall 41 at two opposite sides, an elastic flap 43 mounted in each slot 42, a second positioning flange 44 radially outwardly extending from a top end of the second ring wall 41, and a first external flange 45 extending around the outer surface of the second ring wall 41 at an opposing bottom end thereof. Further, the outer diameter of the second positioning flange 44 is larger than the outer diameter of the first external flange 45. Further, the outer diameter of the first external flange 45 is larger than the inner diameter of the first internal flange 32 of the needle holder 30.

When assembling the barrel 20, the needle holder 30 and the interlocking seat 40, as shown in FIGS. 4, 6, 7 and 7A, insert the needle holder 30 through the opening 22 of the barrel body 21 of the barrel 20 into the inside of the tubular neck 23 of the barrel 20 to expose the tubular wall 36 of the needle holder 30 to the outside of the tubular neck 23 of the barrel 20, then insert the interlocking seat 40 into the inside of the first ring wall 31 of the needle holder 30 to force the first external flange 45 into engagement with the second internal flange 33 of the needle holder 30. At this time, the second positioning flange 44 of the interlocking seat 40 is forced to push the first positioning flange 34 of the needle holder 30, thereby radially deforming the first positioning flange 34 of the needle holder 30 and forcing the first positioning flange 34 to engage into the positioning groove 24 of the barrel 20. Based on this design, the needle holder 30 can be firmly positioned in the tubular neck 23 of the barrel 20 to bear the pressure from the needlestick in the injection.

The plunger 50 is inserted through the opening 22 of the barrel 20 into the inside of the barrel body 21, and can be reciprocated up and down in the barrel 20 by an external force. Further, as shown in FIGS. 1 and 1A, the plunger 50 has a bottom end thereof mounted with an elastic stopper 62. Further, the plunger 50 comprises a pressing portion 51 located at the bottom end thereof and extending out of the elastic stopper 62, and a second external flange 52 extending around the periphery of the pressing portion 51. The outer diameter of the second external flange 52 is larger than the distance between the two elastic flaps 43 of the interlocking seat 40. Further, the elastic stopper 62 comprises a buffer portion 63 protruded from a top end thereof. In this embodiment, the buffer portion 63 is an annular flange located at the top end of the elastic stopper 62. However, this configuration is not a limitation. Alternatively, the buffer portion 63 can be made in the form of a post or any other structure capable of providing a buffering effect.

Figures 7, 7A:
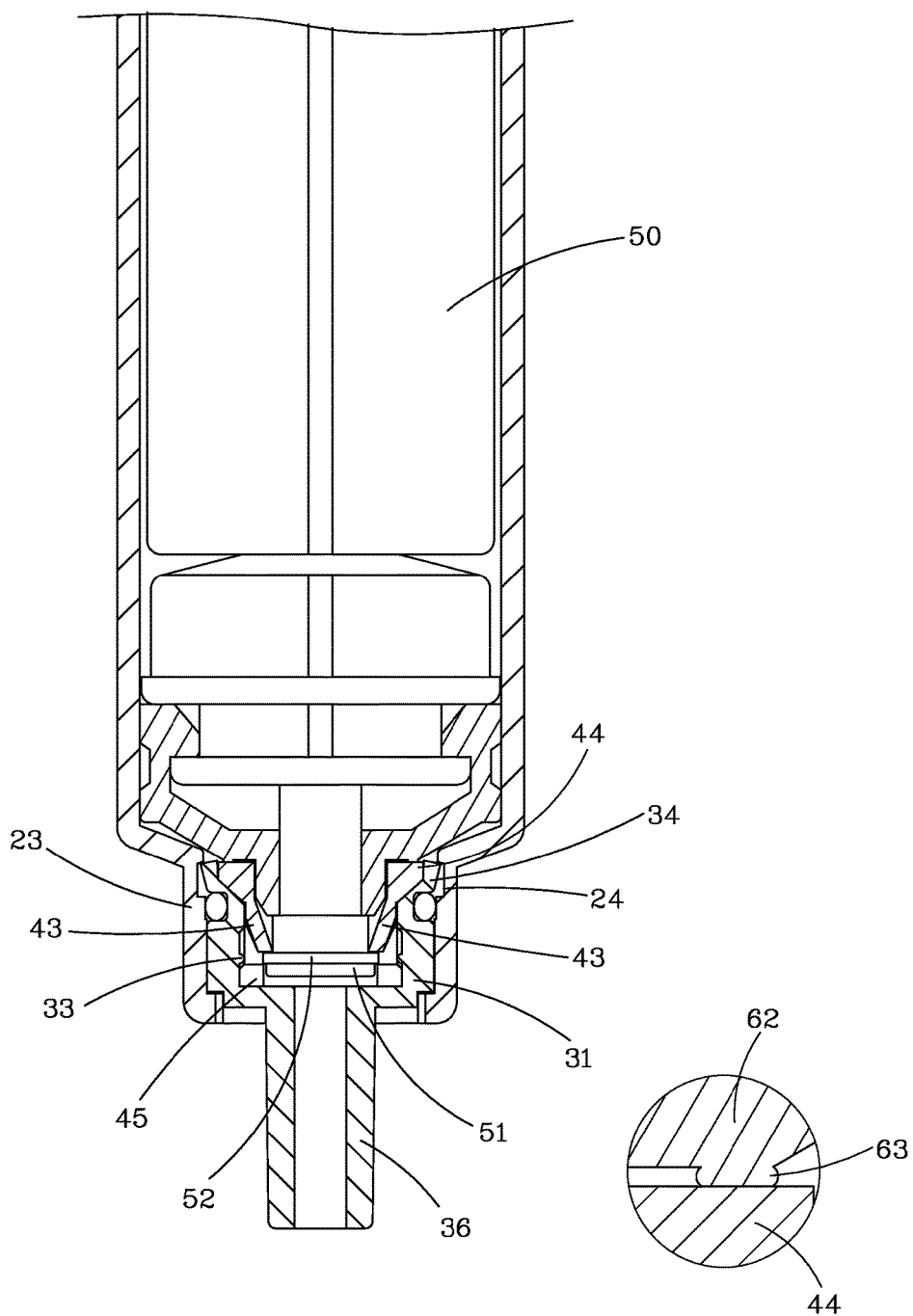
FIG. 7 is a sectional view of a part of the present invention, illustrating the first external flange of the interlocking seat engaged with the second internal flange of the needle holder.
FIG. 7A is an enlarged view of a part of FIG. 7, illustrating the buffer portion stopped at the second positioning flange.

When pushing the plunger 50 forwards in an injection operation, the pressing portion 51 of the plunger 50 will be inserted into the inside of the second ring wall 41 of the interlocking seat 40, and the elastic flaps 43 of the interlocking seat 40 will be stretched open by the second external flange 52 of the plunger 50 for enabling the pressing portion 51 to pass over. After the second external flange 52 passed over the elastic flaps 43 of the interlocking seat 40, the elastic flaps 43 of the interlocking seat 40 immediately return to their former shape subject to their elastic restoring force and are stopped against the second external flange 52 at the pressing portion 51 of the plunger 50, as shown in FIG. 7. When continuously pushing the plunger 50 forwards, the second external flange 52 at the pressing portion 51 of the plunger 50 will be stopped against the first external flange 45 of the interlocking seat 40, and the residual fluid in the needle holder 30 will be minimized subject to the movement of the pressing portion 51 of the plunger 50, thereby finishing the injection. During engagement between the interlocking seat 40 and the plunger 50, the buffer portion 63 at the top end of the elastic stopper 62 provides a buffer stroke so that when the buffer portion 63 is stopped at the second positioning flange 44, it needs to push the plunger 50 further forward to force the second external flange 52 into engagement with the elastic flaps 43.

Figure 8:
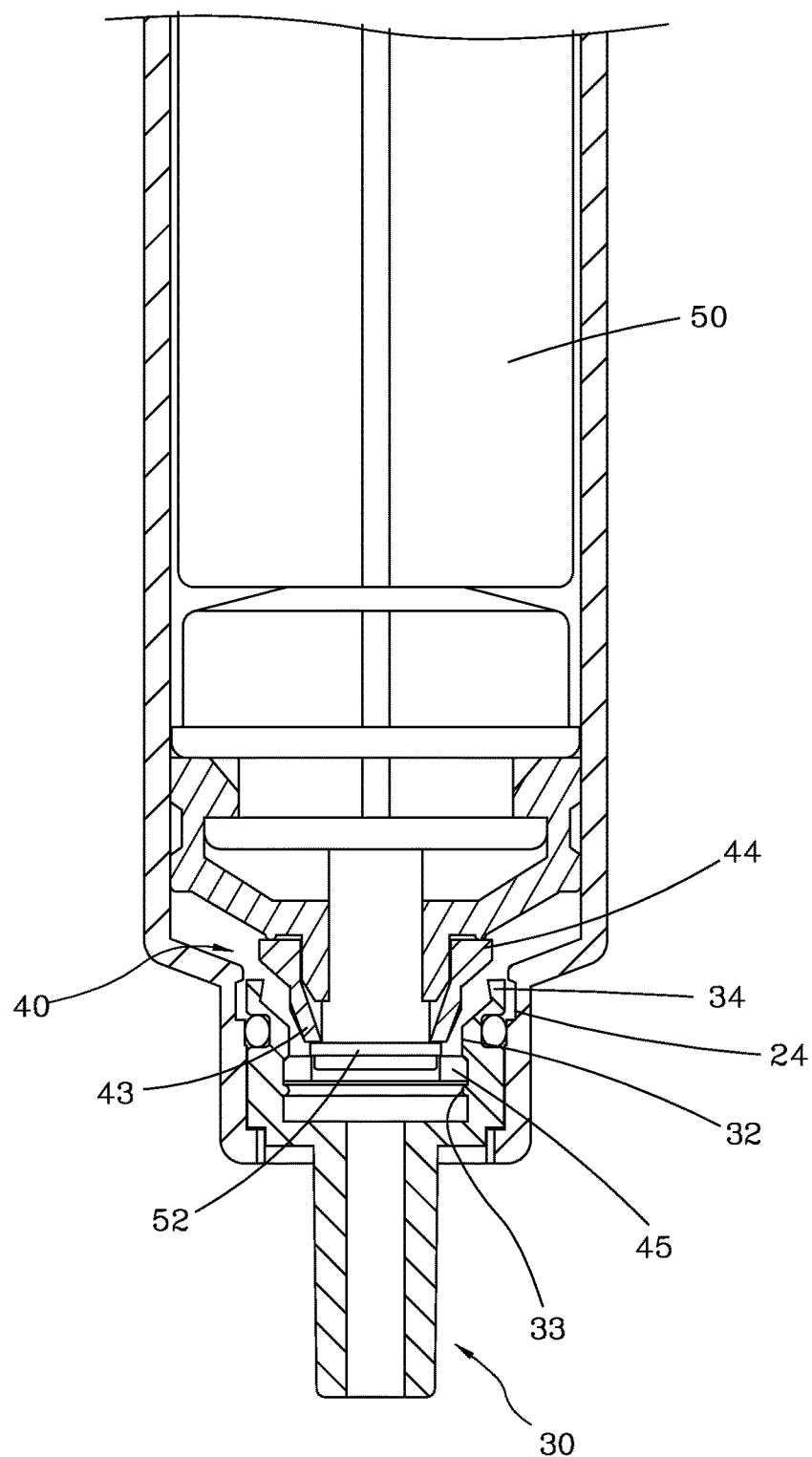
FIG. 8 is similar to FIG. 7, illustrating the first external flange of the interlocking seat engaged with the first internal flange of the needle holder.
Figure 9:
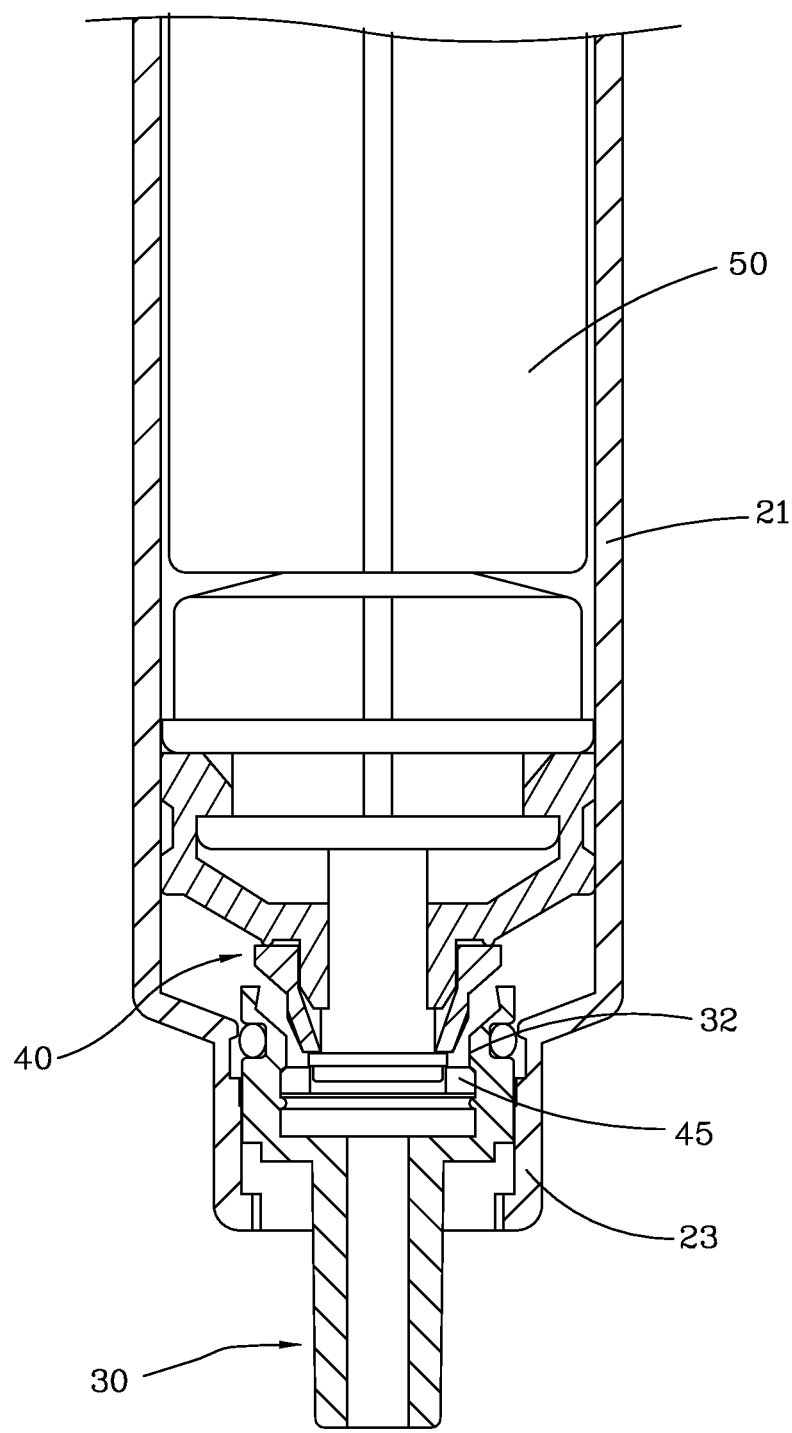
FIG. 9 is similar to FIG. 8, illustrating the needle holder moved with the interlocking seat to the inside of the barrel.

After injection, the medical personnel can pull the plunger 50 backwards. At the time the plunger 50 is pulled backward, as shown in FIG. 8, the interlocking seat 40 and the plunger 50 are engaged together, and the needle holder 30 is secured to the barrel 20, and therefore the first external flange 45 of the interlocking seat 40 will be disengaged from the second internal flange 33 of the needle holder 30 at first upon a backward movement of the plunger 50, enabling the interlocking seat 40 to be moved in direction away from the needle holder 30 to the extent where the first external flange 45 of the interlocking seat 40 is forced into engagement with the first internal flange 32 of the needle holder 30. At this time, the second positioning flange 44 of the interlocking seat 40 is disengaged from the first positioning flange 34 of the needle holder 30 to release the push force of the first positioning flange 34 of the needle holder 30, and thus the needle holder 30 is unlocked. Under this condition, as shown in FIG. 9, when continuously pulling the plunger 50 backwards, due to the engagement relationship between the interlocking seat 40 and the needle holder 30, the needle holder 40 with the attached needlestick can be pulled backwardly away from the tubular neck 23 of the barrel 20 into the inside of the barrel body 21 of the barrel 20 and received therein.

In conclusion, subject to the arrangement and engagement relationship among the needle holder 30, interlocking seat 40 and plunger 50 of the safety syringe 10, the structural stability of the needle holder 30 is maintained and the needle holder 30 will not fall from the barrel 20 accidentally during the injection operation and the amount of residual fluid can be minimized to avoid waste. After the injection, the needle holder 30 with the attached needlestick can be accurately carried by the interlocking seat 40 backwardly into the inside of the barrel 20 when the plunger 50 is pulled back, preventing needlestick injuries and facilitating implementation of single-use. Further, after the plunger 50 is pushed to the end in the injection, the user needs to apply a further push force to the plunger 50 so that the interlocking seat 40 can be pulled backwardly into the inside of the barrel 20. This two-stage force application design avoids accidental engagement between the interlocking seat 40 and the plunger 50 due to the use of unnecessarily excessive force during the injection.

What is claimed is:

1. A safety syringe, comprising:
   a barrel comprising a barrel body, a tubular neck outwardly extending from one end of said barrel body, and a positioning groove extending around an inside wall of said tubular neck;
   a needle holder detachably mounted in said tubular neck of said barrel, said needle holder comprising a first ring wall, a first internal flange, a second internal flange and a first positioning flange, said first internal flange and said second internal flange located in said first ring wall, said first internal flange and said second internal flange being spaced from each other at a predetermined distance, an inner diameter of said first internal flange is smaller than an inner diameter of said second internal flange, said first positioning flange located at one end of said first ring wall and elastically engaged in said positioning groove inside said tubular neck of said barrel;
   an interlocking seat axially movably mounted in said first ring wall of said needle holder, said interlocking seat comprising a second ring wall, a first external flange and a second positioning flange, at least one elastic flap mounted between said first external flange and said second positioning flange in said second ring wall, said first external flange located at one end of said second ring wall for selectively engaging with said first internal flange or said second positioning flange of said needle holder by an axial movement of said interlocking seat, the second positioning flange located at an opposite end of said second ring wall and stopped against said first positioning flange of said needle holder; and
   a plunger axially movably mounted in said barrel body of said barrel, said plunger comprising a pressing portion inserted into the inside of said second ring wall of said interlocking seat and a second external flange located at an outer surface of said pressing portion and adapted for engagement with said elastic flaps of said interlocking seat upon an axial movement of said plunger relative to said barrel.

2. The safety syringe as claimed in claim 1, wherein said needle holder further comprises an end wall and a tubular wall, said end wall being located at an opposite end of said first ring wall remote from said first positioning flange, a distance between said end wall and said second internal flange being smaller than a distance between said end wall and said first internal flange, said tubular wall extending from one end of said end wall to the outside of said tubular neck of said barrel in direction away from said first ring wall.

3. The safety syringe as claimed in claim 1, wherein said interlocking seat further comprises at least one slot located in said second ring wall; each said elastic flap is located in one respective said slot.

4. The safety syringe as claimed in claim 3, wherein said interlocking seat comprises two said slots located in said second ring wall at two opposite sides, each said slot having one said elastic flap located therein, a distance between the two said elastic flaps being smaller than an outer diameter of said second external flange at said pressing portion of said plunger.

5. The safety syringe as claimed in claim 1, wherein an outer diameter of said second positioning flange of said interlocking seat is larger than an outer diameter of said first positioning flange of said needle holder and said second positioning flange of said interlocking seat is forced to push the first positioning flange of said needle holder when said interlocking seat inserting into said needle holder; the outer diameter of said first positioning flange of said needle holder is larger than an outer diameter of said first external flange of said interlocking seat.

6. The safety syringe as claimed in claim 1, wherein said plunger has a bottom end thereof mounted with an elastic stopper, said elastic stopper comprising a buffer portion located at a top end thereof.

\* \* \* \* \*